US006071746A

United States Patent [19]
Seabrook et al.

[11] Patent Number: 6,071,746
[45] Date of Patent: Jun. 6, 2000

[54] REGENERATION OF SOMATIC EMBRYOS FROM PLANT TISSUES

[75] Inventors: Jane Seabrook; L. Katheryn Douglass, both of New Brunswick, Canada

[73] Assignee: Agriculture and Agri-Food Canada, Ontario, Canada

[21] Appl. No.: 09/017,648

[22] Filed: Feb. 2, 1998

[51] Int. Cl.$^7$ .............................. A01H 4/00; C12N 5/04; A01C 1/00

[52] U.S. Cl. ........................ 435/429; 435/420; 435/430; 435/430.1; 435/431; 800/265; 800/268; 800/317.2

[58] Field of Search ................................... 435/420, 429, 435/430, 430.1, 431; 800/265, 268, 317.2

[56] References Cited

U.S. PATENT DOCUMENTS

| | | | |
|---|---|---|---|
| 4,931,394 | 6/1990 | Krul .................................. | 435/240.45 |
| 5,413,929 | 5/1995 | Ishizaki et al. .................... | 435/240.45 |
| 5,498,541 | 3/1996 | Oka et al. .......................... | 435/240.45 |
| 5,530,182 | 6/1996 | Sondahl et al. ......................... | 800/200 |
| 5,681,730 | 10/1997 | Ellis ..................................... | 435/172.3 |

FOREIGN PATENT DOCUMENTS

| | | |
|---|---|---|
| 0 606 759 | 7/1994 | European Pat. Off. . |
| 92/00371 | 1/1992 | WIPO . |
| 97/49277 | 12/1997 | WIPO . |

OTHER PUBLICATIONS

Trigiano et al., Plant Tissue Culture Concepts and Laboratory Exercises, CRC Press, Forida, 1996, p. 138.

Garcia et al., Somatic Embryogenesis in *Solanum tuberosum* L. cv. Desiree from Stem Nodal Sections, Journal of Plant Physiology, (1995) vol. 145, No. 4, pp. 526–530.

Upadhya et al., Potato Tissue Culture and Plantlet Regeneration, Adv. Plant Reprod. Physiol. 1978, pp. 329–339.

Upadhya et al., Potato Tissue Culture and Plantlet Regeration, Physiology of Sexual Reproduction in Flowering Plants, 1976, pp. 489–493.

Hulme et al., An Efficient Genotype–Independent Method for Regeneration of Potato Plants from Leaf Tissue, Plant Cell Tissue and organ Culture, (1992) vol. 31, No. 2, pp. 161–167.

Song et al., Rearing of Disease Resistant Potato by Using Plant Tissue Culture System. (l) Callus Induction and Plant Regeneration from Potato Explants, Memoirs of the Faculty of Agriculture, Kinki University, (1987) No. 20, pp. 1–11.

Kanyand et al., Thidiazuron Promotes High Frequency Regeneration of Peanut (*Arachis hypogaea*) Plants in Vitro. Plant Cell Rep (1994) 14:1–5.

Bragdo–Aas "Regeneration of Plants from Callus of Potato Tubers", *Acta Horticulturae* 78, 1977, pp. 133–137.

Pretova et al., "Somatic Embryogenesis in *Solanum tuberosum* L. cv. Désirée from Unripe Zygotic Embryos", *J. Plant Physiol*, 139:539–542 (1992).

Hutchinson, M.J. et al., Morphoregulatory Role of Thidiazuron: Evidence of the Involvement of Endogenous Auxin in Thidiazuron–induced Somatic Embryogenesis of Geranium (Pelargonium x hortorum Bailey), *J. Plant Physiol.*, 139:539–542 (1992).

Newman, P.O. et al., "Regeneration of Tomato (*Lycopersicon Esculentum* Mill.): Somatic Embryogenesis and Shoot Organogenesis From Hypocotyl Explants Induced With 6–Benzyladenine", *Int. J. Plant Sci.*, 157(5):554–560 (1996).

Hutchinson, M.J. et al., "Morphological and Physiological Changes During Thidiazuron–Induced Somatic Embryogenesis in Geranium (Pelargonium x Hortium Bailey) Hypocotyl Cultures", *Int. J. Plant Sci.*, 157(4):440–446 (1996).

De Garcia, E. et al., "Somatic Embryogenesis in *Solanum tuberosum* L. cv. Désirée from Stem Nodal Sections", *J. Plant Physiol.*, 145:526–530 (1995).

Bajaj, Y.P.S., "Somatic Embryogenesis and Its Applications for Crop Improvement", *Biotechnology in Agriculture and Forestry*, vol. 30, pp. 105–125 (1995).

Bajaj, Y.P.S., "Cryopreservation of Somatic Embryos", *Biotechnology in Agriculture and Forestry*, vol. 30, pp. 221–262 (1995).

Chen, L. et al., Plant Regeneration via Somatic Embryogenesis from Cotyledon Protoplasts of Tomato (*Lycopersicon esculentum* Mill.), *Breeding Science*, 44(3):257–262 (1994).

D'Onghia, A.M., et al., "Somatic Embryogenesis from Style Culture as a Possible Means for Virus Elimination in citrus", *J. Phytopathology*, 145:77–79 (1997).

(List continued on next page.)

*Primary Examiner*—David T. Fox
*Assistant Examiner*—Anne Marie Grünberg
*Attorney, Agent, or Firm*—Testa, Hurwitz & Thibeault, LLP

[57] ABSTRACT

This invention is directed to a method for producing somatic embryos on plant tissue. Furthermore, somatic embryos may be produced using explants obtained from a broad range of plant species, and using either juvenile or mature tissues. The method involves obtaining a stock tissue culture plantlet by exposing the plant tissue to a medium comprising salts, vitamins and an energy source; preparing an explant from the stock tissue culture plantlet; transferring the explant to a proliferation medium comprising salts, vitamins, an energy source and at least one growth regulator for a period of time sufficient to produce a callused explant; and transferring the callused explant to a medium comprising salts, vitamins, an energy source and at least two growth regulators for a period of time sufficient to produce somatic embryos. Following this method somatic embryos are produce in significantly less time that observed using other somatic embryogenesis protocols. Plants produced from the somatic embryos are easily prepared. Since somatic embryos can be obtained from mature tissues, specific plants of agronomic importance comprising desirable traits, may now be clonally propagated. Furthermore, somatic embryos produced following the method of this invention may be used for the preparation of synthetic seed.

9 Claims, 1 Drawing Sheet

OTHER PUBLICATIONS

Ellis, D., "Genetic Transformation of Somatic Embryos", *Biotechnology in Agriculture and Forestry*, vol. 30., pp. 207–220 (1995).

DeGarcia, E., et al., "Somatic Embryogenesis in *Solanum tuberosum* L. cv. Désirée from Stem Nodal Sections", *J. Plant Physiol.*, 145:526–530 (1995).

Gill, R., et al., Somatic Embryogenesis and Plant Regeneration from Seedling Cultures of Tomato (*Lycopersicon esculentum* Mill.), *J. Plant Physiol.*, 147:273–276 (1995).

Gray, D.J., et al., "Somatic Embryogenesis and the Technology of Synthetic Seed", *Biotechnology in Argriculture and Forestry*, vol. 30, pp. 126–151 (1995).

Redenbaugh, K. et al., "Artificial Seeds—Encapsulated Somatic Embryos", Biotechnology in Agriculture and Forestry, vol. 17, pp. 395–416 (1991).

Scorza, R. et al., "Producing Transgenic Thompson Seedless Grap (*Vitis vinifera L.* ) Plants", *J, Americ. Soc. Hort. Sci.*, 121(4):616–619 (1996).

Zhou, X., et al., "Somatic Embryogenesis and Analysis of Peroxidase in Cultured Letuce (*Lattuca sativa* L. ) Cotyledons", *Annals. of Botany*, 69:97–100 (1992).

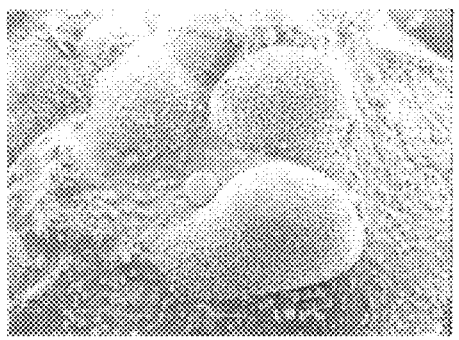
FIG. IA
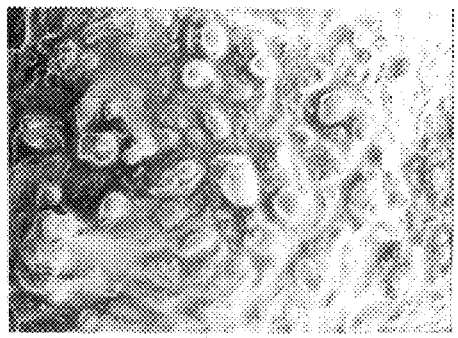
FIG. IB
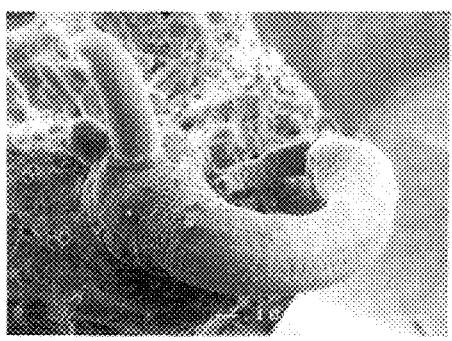
FIG. IC
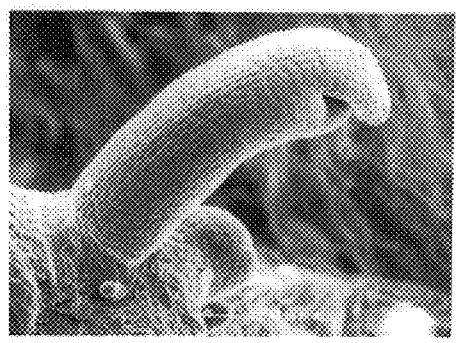
FIG. ID
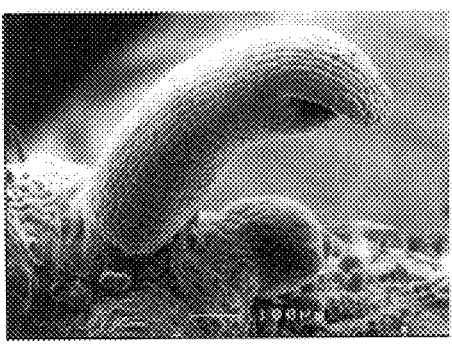
FIG. IE
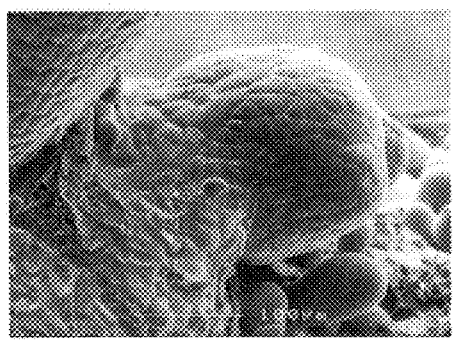
FIG. IF
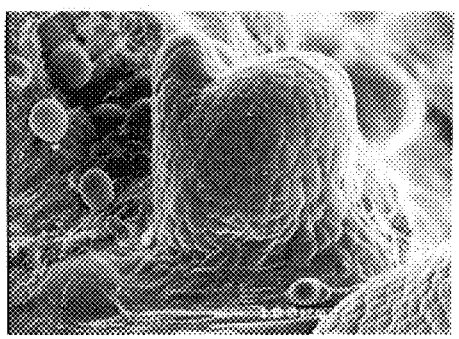
FIG. IG
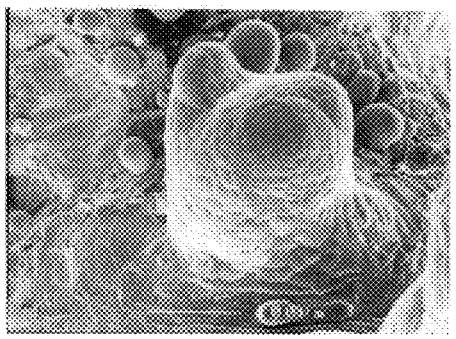
FIG. IH

REGENERATION OF SOMATIC EMBRYOS FROM PLANT TISSUES

The present invention relates to a method for the production of somatic embryos in plants.

BACKGROUND OF THE INVENTION

Somatic embryos are embryos formed in tissue cultures of plants, although there are reports of somatic embryos forming in vivo. The structure and morphology of somatic embryos is like that of zygotic embryos from true seed, that is somatic embryos go through the same development stages—proembryo, globular, heat-shaped and torpedo-shaped morphology. However, somatic embryos lack a seed coat, and also sometimes lack a suspensor. Unless they are specially treated, somatic embryos also lack the dormancy that characterizes true seed (Gray et al., 1995a).

Somatic embryos are clonal in origin and thus multiplication using somatic embryos can have the potential for exceedingly high rates of vegetative increase and is therefore of considerable commercial interest. Somatic embryos also lend themselves to large scale production in bioreactors when grown in liquid culture (Bajaj, 1995a) and this form of propagation is of commercial interest when somatic embryos are transformed to provide novel plant forms.

Regeneration via somatic embryogenesis is an attractive option for plant tissue culture. Somatic embryos reportedly provide more stable regenerants than shoots. Another advantage of regeneration systems using somatic embryos is their apparent single cell origin. This means that it is unlikely that regenerants are of chimerical origin, since, if a regenerant originates from a cluster of cells rather than a single sell, the plant tissues may be chimerical or unstable and produce off-types. The availability of somatic embryogenesis protocols for potato, or other crop species recalcitrant to somatic embryogenesis, will permit these crops to take advantage of any new artificial seed technology advances.

Immature somatic embryos are ideal material for transformation protocols (Ellis, 1995). The induction of somatic embryos from cultured tissues of *Vitus vinifera* (Goussard and Wiid, 1993) and *Citrus* (D'Onghia et al., 1979) has led to the elimination of several viruses and viroids. Scorza et al. (1996) disclose the transformation of somatic embryos of 'Thompson Seedless' grape. The use of somatic embryo technology for potato and other species recalcitrant to somatic embryogenesis, would open new avenues for research and development. As somatic embryos are reported to be more stable regenerants than adventitious shoots, the use of somatic embryos as transformant tissues may overcome the difficulties with off-types which are inherent with the use of stem internode leaf and microtuber tissue. Somatic embryos are suitable for transformation via *Agrobacterium tumefaciens* (Mathews et al., 1992), microinjection (Neuhaus et al., 1987) and particle bombardment (Wilde et al., 1992).

Many plant species regenerate shoots from tissues cultured in vitro, but the low frequency of shoot regeneration and the lack of stability (trueness-to-type) makes this technology less desirable. This is to be contrasted with the proposed somatic embryo technology described herein. This technology is very productive and results in many embryos being regenerated from one explant. Furthermore, this technology can be readily adapted for use with existing or future transformation technologies. Prior to transforming plant tissues with novel genes, a regeneration technology has to be in place or there is no way to recover transformed plants.

Plant tissues regenerated as shoots or somatic embryos in vitro can be used to carry valuable genetic material coding for the production of vaccines, disease resistant plants, superior agronomic characteristics, food processing qualities, etc.

Somatic embryos can be cryopreserved using liquid nitrogen without loss of viability. Cryopreservation is an efficient means of maintaining germplasm and enables plant material to be transported over large distances. Furthermore, somatic embryos are suitable for the development of artificial seed technology (U.S. Pat. No. 5,572,827; Bajaj, 1995 a). Regeneration technologies in which somatic embryos are the propagule can produce many more regenerants and lead the way for the production of artificial seed (synseed) technology. Synthetic seed, appropriately coated with products providing nutrients and protection against desiccation and microorganisms may be used within fluid drilling technology to "sow" the synseeds under field conditions.

Somatic embryos have been produced from juvenile somatic tissues, or from cultured stocks of juvenile tissues, for a few potato cultivars (Bragdø-Aas, 1977; Garcia and Martinez, 1995; Pretova and Dedicova, 1990). Pretova and Dedicova (1992) disclose the production of cotyledonary somatic embryos obtained from zygotic embryo tissues (i.e. juvenile tissues) from potato in media using BAP, dicamba or 2,4-D. They note that friable callus is obtained after 2 weeks. However, a granular callus is not obtained for 6–8 weeks on media containing 2,4-D. After subculturing this callus onto hormone free media supplemented with sucrose, somatic embryos appear within 14–18 days. Bragdø-Aas (1977) discloses the formation of callus from potato tuber tissue and the regeneration of plants from this callus tissue. It is noted that there is great variety in the production of callus depending upon the genetic background of the material used. Furthermore, the applicability of this method is limited to certain clonal sources and therefore lacks applicability to a range of cultivars. Hutchinson et al. (1996) teach the production of somatic embryos using explants obtained from six day old etiolated hypocotyls of geranium. The media contained either TZD, or IAA+BAP, and embryo formation was observed over a 21 day period. The production of embryos was not investigated past the 21 day period.

Garcia and Martinez (1995) disclose the induction of somatic embryos from cultured stem sections of the potato variety 'Bintje'. The protocol employed by these workers requires about 20 to 25 weeks to produce somatic embryos, and another 5 to 6 weeks to produce plantlets from these somatic embryos. However, the method of this invention produces somatic embryos after 4 to 6 weeks, with plantlets forming within 2 to 4 weeks from these somatic embryos. Furthermore, within the prior art, somatic embryos from potato have only been obtained from tetraploid genotypes, however, following the protocol of this invention, somatic embryos have been produced using tetraploid, diploid and monoploid potato cultivars. There are also many other advantages associated with the production of somatic embryos following the method disclosed herein (e.g. see Table 1).

Similarly, somatic embryos from seedling tissues, such as cotyledons, which are juvenile in a physiological sense, of tomato (Chen and Adachi, 1994; Gill et al., 1995) and lettuce (Zhou et al., 1992) have been prepared. Furthermore, somatic embryos have been prepared using hypocotyl sections of juvenile tomato seedlings. However, the ability to produce somatic embryos from mature tissues is in general lacking. This is also true with conifer somatic embryo technology as well, which is directed to juvenile (zygotic embryo) tissues. The preparation of somatic embryos using zygotic (seed) embryos is a common way of achieving embryogenesis. However, this system has the disadvantage that the variability of a heterozygous species produces unreliable propagules for industrial applications.

There is a real need within the art to be able to propagate a plant that has already been selected for a set of desirable traits. Current breeding practices typically require sexual crossing, grafting or other procedures that results in the offspring never being identical to the parent. Since the ability to propagate the exact same individual does not exist with these techniques, a breeder must then rescreen the offspring in order to reselect and validate the stock material for the desired set of characteristics. The ability to propagate a plant comprising the same set of characteristics as the parent, is available through clonal propagation. However, the use of juvenile tissues for the production of somatic embryos, does not improve this situation as the material used for somatic embryogenesis has itself not been subject to the screening process. The ability to produce somatic embryos from mature tissues, however, provides the ability to generate clonal propagules from an individual plant that has been subject to a screening process, so that the propagule comprised the same set of characteristics as the pre-selected parent.

The regeneration of tissues from mature plants of potato, tomato and lettuce via somatic embryogenesis would enable industry to rapidly propagate elite plants of horticultural value. By contrast, propagating tissues from zygotic embryos is not feasible in heterozygous plants such as potato which are vegetatively propagated because of the variability of seedling material. Furthermore, somatic embryos lend themselves to transformation of valuable genotypes.

By using the method of the present invention:

somatic embryos have been obtained on a plurality of potato (*Solanum tuberosum* L.) cultivars, of a variety of ploidy levels in vitro. This protocol can be used for clonal multiplication of selected potato genotypes, regeneration after gene transformation or bombardment, large-scale production of somatic embryos for artificial seed production, etc.;

somatic embryos are obtained within significantly shorter time frames than prior art methods;

somatic embryos can be induced to form on various somatic tissues of the potato, including stem internodes, roots, leaves, microtuber slices;

somatic embryos can be produced on stem internode tissue from plantlets in vitro of tomato;

Somatic embryos have been produced on seedling leaf and stem tissue of lettuce in vitro. Somatic Embryos have also been produced on mature tissues of lettuce in vitro. This is of commercial interest because superior genotypes can be multiplied clonally.

SUMMARY OF THE INVENTION

The present invention relates to a method for the production of somatic embryos in plants.

The method of the present invention involves the use of several different culture media and the brief exposure of a tissue explant to these media. By so doing, the overall time required to obtain somatic embryos is dramatically reduced, and somatic embryos can be produced from typically recalcitrant species. Furthermore, somatic embryos can be prepared from mature tissues in a wide variety of species.

According to the present invention there is provided a method (A) for producing somatic embryos on plant tissue comprising: obtaining a stock tissue culture plantlet by exposing the plant tissue to a medium (medium #1) comprising salts, vitamins and an energy source; preparing an explant from the stock tissue culture plantlet; transferring the explant to a proliferation medium (medium #2) comprising salts, vitamins, an energy source and at least one growth regulator for a period of time sufficient to produce a callused explant; and transferring the callused explant to a medium (medium #3) comprising salts, vitamins, an energy source and at least two growth regulators for a period of time sufficient to produce somatic embryos.

This invention is also directed at a method as described above, wherein the stock tissue culture plantlet is maintained from about 4 to about 5 weeks prior to transfer to the proliferation medium. This invention is encompasses the above method, wherein the period of time the explant is maintained in the proliferation medium is from about 1 to about 4 weeks, and wherein the period of time within the medium comprising at least two growth regulators is from about 2 to about 6 weeks.

This invention also provides a method as described above, wherein the growth regulator of the proliferation medium is selected from the group consisting of Thidiazuron, BAP, or Indole acetic acid, or a combination thereof Furthermore, the growth regulators within the medium comprising at least two growth regulators are selected from the group consisting of Zeatin, Indole acetic acid, or Gibberellic acid, or a combination thereof This invention also embraces the above method wherein the plant tissue is obtained from potato, tomato or lettuce, and wherein the plant tissue is obtained from mature tissue including stem internode, root, leaf, microtuber tissue, leaf, or axilary bud tissue.

This invention is also directed to the above method wherein the somatic embryo is grown into a plant, cryopreserved, or treated for use as a synthetic seed.

This invention also provides for a somatic embryo produced using the method as described above, as well as a plant obtained using a somatic embryo obtained using the method described above.

Furthermore, this invention describes a method (B) of maintaining a plant comprising a desired set of characteristics comprising: screening a library of plants for a desired set of characteristics; selecting a plant having the desired set of characteristics; preparing a somatic embryo, from tissue obtained from the selected plant, using the method (A); and either storing the somatic embryo, or growing the somatic embryo into a plant.

This invention also encompasses a method of obtaining a transgenic plant with a desired set of characteristics comprising: transforming a plant with a gene of interest; screening transformed plants to obtain a plant with the desired set of characteristics; obtaining an explant from the transformed plant; and preparing somatic embryos using the method (A) as defined above. Also considered within the scope of the present invention is a method of preparing a transgenic plant comprising: preparing somatic embryos according to the method (A) defined above; introducing a gene of interest into the somatic embryo; screening the transformed somatic embryos for the presence of the transgene; growing the selected somatic embryo into a plant; and optionally, propagating the selected somatic embryo or plant.

This invention is directed at a method (A) for producing somatic embryos as defined above wherein:

the stock tissue culture plantlets are maintained on a medium (Medium #1) comprising:

| Murashige and Skoog salts, full strength | |
|---|---|
| sucrose | 30 g/l |
| myo-inositol | 100 g/l |
| vitamins | |
| Nicotinic acid | 0.5 mg/l |
| Pantothenic acid | 2.5 mg/l |
| Pyridoxine.HCl | 1.0 mg/l |
| Thiamine.HCl | 0.5 mg/l |
| pH5.8 | |
| agar | 8 g/l; | the proliferation medium, medium #2, comprises:

| Murashige and Skoog salts, full strength | |
|---|---|
| sucrose | 30 g/l |
| myo-inositol | 100 mg/l |
| vitamins | |
| Nicotinic acid | 0.5 mg/l |
| Pantothenic acid | 2.5 mg/l |
| Pyridoxine | 1.0 mg/l |
| Thiamine.HCl | 0.5 mg/l |
| pH 5.8 | |
| Agar | 6.5 g/l; | and further comprises the constituents selected from the group consisting of;

| Medium 2a: | |
|---|---|
| Thidiazuron | 0.15 μM |
| Indole acetic acid | 19 μM; |
| Medium 2b | |
| Thidiazuron | 0.15 μM; |
| Medium 2c | |
| BAP | 0.15 μM |
| IAA | 19 μM; or |
| Medium 2d | |
| BAP | 0.15 μM; | and the medium comprising at least two growth regulators, medium #3, comprises:

| Murashige and Skoog salts, full strength | |
|---|---|
| sucrose | 30 g/l |
| myo-inositol | 100 mg/l |
| vitamins | |
| nicotinic acid | 1.0 mg/l |
| thiamine.HCl | 0.5 mg/l |
| pantothenic acid | 0.5 mg/l |
| pyridoxine | 1.0 mg/l |
| Zeatin | 12.0 μM |
| Indole acetic acid | 0.05 μM |
| Gibberellic acid | 0.55 μM |
| pH 5.8 | |
| agar | 8 g/l |

Many advantages are noted between the above described method and variations thereof, and prior art methods for obtaining somatic embryos. These advantages include:

obtaining somatic embryos within shorter time frames than prior art methods (weeks to months shorter than previously published methods);

adaptability to a range a wide variety of plant species, and cultivars that typically have not been amenable to the production of somatic embryos;

effectiveness in obtaining somatic embryos from both mature or juvenile tissues. Prior art methods are typically limited to juvenile tissues;

with regards to potato cultivars, somatic embryos have been produced using tetraploid, diploid and monoploid tissues. All prior art methods have only been successful using tetraploid tissues, and, to the best of our knowledge, no somatic embryos have previously been reported using diploid or monoploid potato tissues. As a results of these advantages, mature plants may be selected for desirable properties and clonally propagated to ensure maintenance of the genotype and phenotype of the stock tissues. This last advantage has not been previously available within this field since prior art methods for obtaining somatic embryos require juvenile tissues. Any selection of plants with desirable traits, therefore had to place using plants obtained from somatic embryos. This requires producing large amounts of somatic embryos from which plants are regenerated, and the screening of these libraries of regenerated plant stocks.

BRIEF DESCRIPTION OF THE DRAWINGS

These and other features of the invention will become more apparent from the following description in which reference is made to the appended drawings wherein:

FIGS. 1A–1H are a composite print of somatic embryos forming on potato (Solanum tuberosum L.) cultivar 'Russet Burbank'.

FIG. 1A—non-embryogenic callus cells;

FIG. 1B—overview of non-embryogenic callus;

FIG. 1C—germinating somatic embryo with two additional somatic embryos forming at basal area;

FIG. 1D—torpedo stage somatic embryo with hear-shaped somatic embryo forming nearby;

FIG. 1E—slightly different view of embryos in plate FIG. D;

FIG. 1F—detail of heart-shaped somatic embryo shown in FIG. 1D and FIG. 1E, note large callus cells nearby;

FIG. 1G and FIG. 1H—late heart-shaped somatic embryo showing unequal sized cotyledons and external arrangement of epidermal cells.

DESCRIPTION OF PREFERRED EMBODIMENT

The present invention relates to a method for the production of somatic embryos in plants.

Following the method of this invention, somatic embryos are observed using mature tissues as the material from which somatic embryos are produced. Somatic embryos have been obtained using a large range of potato germplasm as well as several other species of plants, for example but not limited to, tomato (all genotypes tested) and lettuce (all genotypes tested). Furthermore, preliminary tests indicate that other species are amenable to the production of somatic embryos following the method of this invention. Globular, heart-shaped and torpedo somatic embryos are observed in all cultures, and embryos excised from these embryos have been grown as plants. Emblings and fully established plants are easily grown from somatic embryos produced using the method of this invention. An analysis of plants regenerated from emblings (that is the small plantlet grown from a somatic embryo) indicates that off-types are not always observed. However, the frequency of observed off-types appears to be influenced by the genotype from which the somatic embryo was obtained, since several genotypes exhibited higher rates of off-types than others.

The method of this invention involves the exposure of explant tissues to short-period treatments of at least two media formulations comprising different compositions of growth regulators. As a result of the use of the method described herein, somatic embryos are obtained within significantly shorter time-frame than prior art methods. Furthermore, the present method is readily adaptable to a range of plant species and cultivars that other wise have not been amenable to the production of somatic embryos, and has proven effective using both mature or juvenile tissues in order to produce somatic embryos. Furthermore, reculture of somatic embryos is possible using the method of this invention.

The basic method is outlined below, however, it is to be understood that variations within this method are readily within the skill of one of skill within the art, and alterations and variations to the over all protocol of this invention are to be considered within the scope of the method disclosed below. In order to exemplify the method and possible medium compositions used, the production of somatic embryos from potato is first outlined, however, variations in this protocol have also been successfully used to obtain somatic embryos from a range of potato cultivars including tetraploid, diploid and monoploid mature tissue, as well as several cultivars of tomato and lettuce.

Induction of Somatic Embryos of Potato

Somatic embryos have been obtained from juvenile potato tissue within the prior art (Petrova and Dedicova, 1992) as well as cultured plant material (Garcia and Martinez, 1995), however, the protocol used is time consuming. For example Garcia and Martinez report that their method requires about 20 to 25 weeks, that is, 5 weeks for callus formation, 12 weeks for embryogenic callus formation and a further 8 weeks for high frequency somatic embryo production in potato (see page 529 of Garcia and Martinez, 1995). Furthermore, their method and has several drawbacks including abnormal embryo development. The method of this invention produces high frequency embryos in potato within 4 to 6 weeks, with no abnormal embryo development. Other comparisons are provided in Table 1, below.

Stock Material for Excision of Explants

Stock tissue culture plantlets of potato cultivars may be propagated using any suitable means. For example, cultivars may be propagated by single-node cuttings established from shoot tips excised from potato sprouts, or root, leaf or microtuber tissues. Cultures are grown in vitro under any suitable day/night regime, and the growth temperature should be maintained from about 12° C. to about 23° C. Without wishing to limit the method of this invention in any manner, the following conditions have proved to be suitable for the preparation of stock material:

- standard cool white fluorescent lamps supplying a suitable light intensity, for example of 25 w/m$^2$
- a day/night regime comprising 16 hour photoperiod, 8 hour dark period
- a growth temperature of 19° C.±1. The basal culture medium can be selected from several available within the art, for example Murashige and Skoog (1962), however, other media as known to those of skill in the art may also be used. For example suitable media may include White's Medium (White 1963), or Linsmayer and Skoog's medium (Linsmayer and Skoog 1965) or the like may also be used. This medium should comprise a salt solution, vitamins, and an energy source, for example sucrose, with no added growth regulators. The following medium (Medium #1), which is not to be considered limiting in any manner, may be used to culture the stock plants from which the subsequent explant material such as a stem intenode explants (or root, leaf, or microtuber derived explants), are obtained.

| Medium #1 | |
|---|---|
| Murashige and Skoog (1962) salts, full strength | |
| energy source, sucrose | 30 g/l |
| myo-inositol | 100 g/l |
| vitamins | |
| Nicotinic acid | 0.5 mg/l |
| Pantothenic acid | 2.5 mg/l |
| Pyridoxine.HCl | 1.0 mg/l |
| Thiamine.HCl | 0.5 mg/l |
| pH 5.8 | |
| TC agar (JRH Biosciences Ltd.) | 8 g/l |

Induction of Nodular Callus

When stock plantlets have been incubated under the above conditions from about 2 to about 20 weeks, or preferably from about 3 to about 10 weeks, or more preferably, from about four to about five weeks, sections of stem internode are excised aseptically and placed onto Proliferation medium (medium #2). The length of stem internode may vary per cultivar used, a suitable length, for example, may be from about 0.5 to about 1.5 cm. Best results in producing the maximum number of somatic embryos per explant are observed if healthy, vigorous stock tissue culture plantlets material is used.

The proliferation medium, medium #2, is typically a semi-solid medium, however, other media exhibiting a range of consistencies may also be found to be effective. Suitable proliferation media, without intending to limit the use of other media for this purpose, may comprise Thidiazuron or BAP, and optionally Indole acetic acid. Several compositions of Medium 2 are listed below as examples of Proliferation media, however, variations of the composition of medium #2 have been found to be effective in producing somatic embryos with different cultivars (see Medium 2 a to 2 d—below), therefore, other variations of the composition of medium #2 may also be effective as a proliferation medium:

| Medium #2, Proliferation Medium | |
|---|---|
| Medium 2a | |
| Murashige and Skoog (1962) salts, full strength | |
| energy source, sucrose | 30 g/l |
| myo-inositol | 100 mg/l |
| vitamins | |
| Nicotinic acid | 0.5 mg/l |
| Pantothenic acid | 2.5 mg/l |
| Pyridoxine | 1.0 mg/l |
| Thiamine.HCl | 0.5 mg/l |
| *Thidiazuron | 0.15 µM |
| *Indole acetic acid | 19 µM |
| pH 5.8 | |
| TC Agar | 6.5 g/l |

-continued

| Medium #2, Proliferation Medium | |
|---|---|
| Medium #2b | |
| Murashige and Skoog (1962) salts, full strength | |
| energy source, sucrose | 30 g/l |
| myo-inositol | 100 mg/l |
| vitamins | |
| nicotinic acid | 0.5 mg/l |
| pantothenic acid | 2.5 mg/l |
| pyridoxine | 1.0 mg/l |
| thiamine | 0.5 mg/l |
| *Thidiazuron | 0.15 μM |
| pH 5.8 | |
| TC agar | 65. g/l |
| Medium #2c | |
| Murashige and Skoog (1965) salts, full strength | |
| energy source, sucrose | 30 gl |
| myo-inositol | 100 mg/l |
| vitamins | |
| nicotinic acid | 0.5 mg/l |
| pantothenic acid | 2.5 mg/l |
| pyridoxine | 1.0 mg/l |
| thiamine | 0.5 mg/l |
| *BAP | 0.15 μM |
| *IAA | 19 μM |
| pH 5.8 | |
| TC agar | 6.5 g/l |
| Medium #2d | |
| Murashige and Skoog (1965) salts, full strength | |
| energy source, sucrose | 30 g/l |
| myo-inositol | 100 mg/l |
| vitamins | |
| nicotinic acid | 0.5 mg/l |
| pantothenic acid | 2.5 mg/l |
| pyridoxine | 1.0 mg/l |
| thiamine | 0.5 mg/l |
| *BAP | 0.15 μM |
| pH 5.8 | |
| TC agar | 6.5 g/l |

*Filter sterilized

Explants are maintained on medium #2 from about 3 days to about 4 weeks, or more preferably from about 6 to 15 days. A suitable time for maintaining explants on this medium, which should not be considered limiting in any manner, is of about 7 days. Tissues maintained on medium #2 increase in size, and the cut surfaces of the tissues has been found to suberize. Routinely, an increase in size of about five-fold is observed. A nodular, callus forms on the cut surface of the explants, typically in 1 to 2 weeks after incubation on medium #2.

Following this step, the explants are transferred to medium #3. An example of Medium # is described below, however, variations in the composition of this medium may be used and this composition is not to be considered limiting in any manner:

| Medium #3 | |
|---|---|
| Murashige and Skoog (1962) salts, full strength | |
| energy source, sucrose | 30 g/l |
| myo-inositol | 100 mg/l |
| vitamins | |
| nicotinic acid | 1.0 mg/l |
| thiamine.HCl | 0.5 mg/l |

-continued

| Medium #3 | |
|---|---|
| pantothenic acid | 0.5 mg/l |
| pyridoxine | 1.0 mg/l |
| *Zeatin | 12.0 μM |
| *Indole acetic acid | 0.05 μM |
| *Gibberellic acid | 0.55 μM |
| pH 5.8 | |
| TC agar | 8 g/l |

*Filter sterilized

Somatic embryos typically form from about two to about six weeks after explants are transferred to medium #3, and have been observed first on the edge of cut surfaces and then to form over the callused cut surface. Following the above protocol, over 100 somatic embryos per 1 cm of stem internode tissue have been observed.

It is preferred that fresh explant material be cultured to produce more embryos, however, embryogenic callus may be subcultured to produce somatic embryos if required.

A comparison of the method of this invention with that of the prior art is provided in Table 1.

TABLE 1

Comparison between the method of this invention and a prior art method on somatic embryogenesis of potato (*Solanum tuberosum* L.).

| CHARACTERISTIC | Garcia AND Martinez | Method of this invention |
|---|---|---|
| Stock material | Tissue culture plantlets | Tissue culture plantlets |
| Nutrient media for stock plantlets | MS salts, vitamins, GA$_3$, 0.1 mg/l., 2.5 g/l sucrose | MS salts, vitamins, no growth regulators, 30 g/l sucrose (medium #1) |
| Explant tissue | Nodal sections (i.e. sections of tissue including the axillary bud subtended by leaf petiole) of mature in vitro plantlets established in vitro, close to shoot apex | Internodal sections of mature in vitro plantlets established in vitro for 2 years, responsive explants are excised from anywhere along the plantlet. Formation of somatic embryos mostly on lower portion (distal) of internode stem section, although this appears to be under genotypic control. Somatic embryos also from on leaf, root and microtuber (in vitro formed tubers) - although somewhat less frequently. |
| Callus phase | 5 weeks for callus formation | callus formation in 1–2 weeks on medium #2. |
| Callus morphology | Callus was friable & green for first month, then became "compact, lobate & brownish" | Callus is nodular, light green to yellow, compact, and forms directly on cut end of stem internodes. |
| Culture media | Solidified with gelrite (a resin gum) | Solidified with agar (natural product) |
| Media components | Induction medium: MS, 2,4-D2.0 mg/l (0.15 μM) and yeast extract. Multiplication medium: MS 2 mg/l 2,4D, yeast extract Differentiation medium: MS GA, (0.1 mg/l) or BA (1 mg/l) - no 2,1D nor yeast extract. | Medium #2: Thidiazuron or BAP (0.15 μM); with or without Indole acetic acid (19 μM). Medium #3 Zeatin (12 μM); IAA (50 nM); GA, (550 nM) |
| Somatic embryo | Report that three | Somatic embryo |

TABLE 1-continued

Comparison between the method of this invention and a prior art method on somatic embryogenesis of potato (Solanum tuberosum L.).

| CHARACTERISTIC | Garcia AND Martinez | Method of this invention |
|---|---|---|
| formation | months is required to produce embryogenic callus. Two more months for high frequency somatic embryo production. | observed after 2–4 weeks on medium #3. High frequency somatic embryo formation immediately for most cultivars tested. Genotypic variability for time to embryo formation and numbers of embryos. |
| Cultivars reported to form somatic embryos in culture | Désirée, | AC Novachip, Atlantic Brador, Caribe, Désirée,, Katahdin, Kennebec, Royal Gold, Ruby Gold, Russet Burbank, Russet Norkotah, Saginaw Gold, Shepody, Superior, Temagami Yukon Gold, F80054, F83065. Somatic embryos have been observed on every cultivar tested. |
| Synchrony of development | Non-synchronous development reported. | Some synchrony observed. But all three development stages (globular, heart-shaped and torpedo) can be found at one time |
| Secondary somatic embryo formation | Secondary somatic embryos observed on hypocotyl of torpedo-shaped somatic embryos. | No secondary embryos observed. |
| Developmental stages | All developmental stages reported. Somatic embryos appear to be embedded in surrounding tissues - no suspensor-like structure observed. | All developmental stages observed. Somatic embryos appear to be embedded in surrounding tissues - no suspensor-like structures observed. |
| Abnormalities | Some abnormal somatic embryos reported in cultures. Necessary to transfer all three stages to MS medium with no growth regulators for normal development of 'emblings' in plantlets. | No abnormal somatic embryos observed. Mature somatic embryos (late torpedo state, sometimes curved like zygotic embryos) when transferred onto MS growth regulator-free medium develop into emblings which resemble morphology of potato seedlings. |
| Embling development from somatic embryos | Emblings develop into plantlets (presumably in vitro) after 45 days. | Emblings develop into plants in vitro rapidly. From globular embryo to 1 cm high embling takes 2–4 weeks. |
| Environmental conditions for tissue culture | Temperature: 23 C. ± 1 Light: continuous light Light intensity: 50 $\mu$mol m$^{-2}$ s$^{-1}$ | Temperature: 19 C. ± 1 Light: 16 h photoperiod Light intensity: 120 $\mu$mol $^{-2}$ s$^{-1}$ provided by Cool-white and Agrolite fluorescent lamps (1:1) |
| Root development on explants | No reported | Explants will produce many roots if left on medium #1 more than 5–10 days. This is cultivar dependent. Presence of root initials appears to be no problem on explants producing somatic embryos because roots do not develop on medium #2. |

Somatic embryos produced using the method of this invention may be stored or manipulated for the generation of emblings and fully established plants (see below). If desired, somatic embryos may be cryopreserved using established techniques (e.g. Bajaj et al., 1995b), or dried and encapsulated with a synthetic endosperm and used as synthetic seed for mechanical handling and planting (e.g. Bajaj 1995 a; Litz and Gray, 1995; Senaratna, 1992; Redenbaugh et al., 1991 and 1992). The ability to maintain somatic embryos for long periods of time helps in ensuring a constant supply of germplasm of agronomically important species.

Furthermore, the maintenance, and propagation of transgenic plants, comprising a gene of interest is feasible using the method described herein. Following the transformation of a plant using standard transformation protocols (e.g. Agrobacterium mediated transfer, particle bombardment etc.), desired plants may be propagated via somatic embryogenesis using the method described herein. This method would involve:

i) transforming a plant with a gene of interest;
ii) screening transformed plants to obtain a plant with the desired set of characteristics;
iii) obtaining an explant from the transformed plant; and
iv) preparing somatic embryos using the method of this invention as described above.

Somatic embryos may themselves be used for the preparation of a transgenic plant using established protocols including Agrobacterium (Mathews et al., 1992), microinjection (Neuhaus et al., 1987), particle bombardment (Wilde et al., 1992) or other protocols as would be evident to one of skill in the art. This method would involve:

i) preparing somatic embryos according to the method of this invention;
ii) introducing a gene of interest into the somatic embryo;
iii) screening the transformed somatic embryos for the presence of the gene of interest;
iv) growing the selected somatic embryo into a plant; and optionally
v) propagating the selected somatic embryo or plant.

To aid in identification of transformed plant cells, constructs comprising the gene of interest may include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS ($\beta$-glucuronidase), or luminescence, such as luciferase are useful.

Regeneration of Somatic Embryos

After a short incubation period of one to two weeks on medium #2 (described above), tissues are transferred to medium #3 (which is also termed Regeneration medium) comprising Zeatin, indole acetic acid, Gibberellic acid, solidified with agar (see above). Note that auxin can be omitted from medium #2. Somatic embryos generally form in 2 to 4 weeks of incubation of medium #3. We have observed that some cultivars of potato are slower to respond than others (e.g. Shepody'). Both distal and proximal cut surfaces of the stem internode explants may produce somatic embryos, but they are more prevalent on the distal (lower) surface, although this may be cultivar dependent. Occasionally, somatic embryos will form on the lateral surface of the stem explants.

Regeneration of Somatic Embryos—Genotypic Differences

All potato cultivars, including tetraploid (48 chromosomes), diploid (24 chromosomes) and monoploid (12 chromosomes) of selected Solanum genotypes, obtained and publicly available from the Fredericton Research Centre, tested to date have regenerated somatic embryos in vitro. To the best of our knowledge, no previous report has been found in the literature reporting the induction of somatic embryos on potato germplasm with less than the tetraploid complement of 48 chromosomes.

Without wishing to be bound by theory, it appears that the productivity of somatic embryos is under genetic control. The time to form somatic embryos, the number of explants responding to induction techniques, and the number of somatic embryos per explant all vary with the cultivar tested.

Clonal differences in the number of stem internodes which produced somatic embryos are also evident (Tables 2 and 3). Most cultivars produce somatic embryos on all explants, but potato cultivars Caribe (22%), Ruby Gold (9%), Shepody (9%), Temagami (17%), and Yukon Gold (51%) have been observed to only produce somatic embryos on a portion of the cultured explants (Table 2 and 3). Changes in media formulation may be required to enhance or produce somatic embryos on some potato cultivars, such minor modifications would be evident to one of skill in the art. For instance, Ruby Gold and Temagami form more somatic embryos when placed on medium 2b (described above).

Previous workers have reported that auxin is mandatory for the induction of somatic embryos in most plant systems (e.g. Raghavan 1986). However, the results presented herein demonstrate that auxin is not required in all stages of this process. For example, medium #2, lacking auxin is effective in producing somatic embryos. Furthermore, several cultivars produce more somatic embryos if medium #2 lacks auxin (e.g. Royal Gold, Ruby Gold and Temagami).

TABLE 2

Number of embryos produced per stem internode explant of potato (*Solanum tuberosum* L) in vitro on medium #2 (one week) and 3 (9 weeks).

| Cultivar | Number of Explants with Embryos | Mean Number of Embryos per Explant |
|---|---|---|
| AC Novachip | 139/140 | 13.6 ± 8.6 |
| Atlantic | 119/119 | 15.9 ± 8.3 |
| Brador | 120/120 | 23.1 ± 11.2 |
| Caribe | 38/109 | 6.5 ± 7.8 |
| Désirée, | 40/40 | 36.1 ± 20.7 |
| F80054 | 110/110 | 25.1 ± 18.7 |
| F83065 | 123/123 | 44.5 ± 23.5 |
| Katahdin | 134/147 | 14.3 ± 9.8 |
| Kennebec | 156/160 | 10.2 ± 6.7 |
| Royal Gold | 24/30 | 17.4 ± 12.2 |
| Ruby Gold | 3/32 | 3.0 ± 2.2 |
| Russet Burbank | 72/72 | 28.4 ± 17 |
| Russet Norkotah | 111/127 | 10.5 ± 8.8 |
| Saginaw Gold | 102/113 | 8.5 ± 6.2 |
| Shepody | 17/120 | 3.9 ± 4.0 |
| Superior | 121/121 | 10.7 ± 5.9 |
| Temagami | 35579 | 4.1 ± 3.2 |
| Yukon Gold | 58/114 | 2.2 ± 1.8 |

TABLE 3

Somatic embryo production on stem internode explants of various cultivars of potato (*Solanum tuberosum* L.) in vitro over 10 weeks. Explants were placed on Medium 1 for 1 week and then transferred to Medium 2 for the remaining 9 weeks.

| Weeks on Media | 1 | 2 | 3 | 4 | 5 | 6 | 7 | 8 | 9 | 10 |
|---|---|---|---|---|---|---|---|---|---|---|
| AC Novachip | | | | | | | | | | |
| # Explants with Embryos | 0 | 0 | 35/140 | 106/140 | 125/140 | 139/140 | 139/140 | 139/140 | 139/140 | 139/140 |
| % Explants with Embryos | 0 | 0 | 25% | 75.7% | 89.3% | 99.3% | 99.3% | 99.3% | 99.3% | 99.3% |
| Atlantic | | | | | | | | | | |
| # Explants with Embryos | 0 | 0 | 2/119 | 87/119 | 119/119 | 119/119 | 119/119 | 119/119 | 119/119 | 119/119 |
| % Explants with Embryos | 0 | 0 | 1.7% | 73.1% | 100% | 100% | 100% | 100 | 100% | 100% |
| Brador | | | | | | | | | | |
| # Explants with Embryos | 0 | 0 | 0 | 83/150 | 114/120 | 120/120 | 120/120 | 120/120 | 120/120 | 120/120 |
| % Explants with Embryos | 0 | 0 | 0 | 55% | 83.3% | 100% | 100% | 100% | 100% | 100% |
| Caribe | | | | | | | | | | |
| # Explants with Embryos | 0 | 0 | 0 | 1/111 | 1/111 | 3/111 | 4/109 | 11/109 | 21/109 | 25/109 |
| % Explants with Embryos | | | | .9% | .9% | 2.7% | 3.7% | 10.1% | 19.3% | 22.9% |
| Désirée, | | | | | | | | | | |
| # Explants with Embryos | 0 | 0 | 0 | 5/40 | 40/40 | 40/40 | 40/40 | 40/40 | 40/40 | 40/40 |
| % Explants with Embryos | | | | 12.5% | 100% | 100% | 100% | 100% | 100% | 100% |

TABLE 3-continued

Somatic embryo production on stem internode explants of various cultivars of potato (*Solanum tuberosum* L.) in vitro over 10 weeks. Explants were placed on Medium 1 for 1 week and then transferred to Medium 2 for the remaining 9 weeks.

| Weeks on Media | 1 | 2 | 3 | 4 | 5 | 6 | 7 | 8 | 9 | 10 |
|---|---|---|---|---|---|---|---|---|---|---|
| F80054 | | | | | | | | | | |
| # Explants with Embryos | 0 | 0 | 0 | 14/110 | 92/110 | 109/110 | 110/110 | 110/110 | 110/110 | 110/110 |
| % Explants with Embryos | 0 | 0 | 0 | 12.7% | 83.6% | 99.1% | 100% | 100% | 100% | 100% |
| F83065 | | | | | | | | | | |
| # Explants with Embryos | 0 | 0 | 0 | 8/125 | 16/125 | 53/125 | 81/125 | 122/123 | 123/123 | 123/123 |
| % Explants with Embryos | 0 | 0 | 0 | 6.5% | 12.8% | 42.4% | 64.8% | 99.2% | 100% | 100% |
| Katahdin | | | | | | | | | | |
| # Explants with Embryos | 0 | 0 | 1/147 | 116/147 | 125/147 | 128/147 | 134/147 | 134/147 | 134/147 | 134/147 |
| % Explants with Embryos | 0 | 0 | .7% | 78.9% | 85% | 87% | 91.2% | 91.2% | 91.2% | 91.2% |
| Kennebec | | | | | | | | | | |
| # Explants with Embryos | 0 | 0 | 29/160 | 117/160 | 147/160 | 151/160 | 156/160 | 156/160 | 156/'60 | 156/160 |
| % Explants with Embryos | 0 | 0 | 18.1% | 73.1% | 91.8% | 94.3% | 97.5% | 97.5% | 97.5% | 97.5% |
| Royal Gold | | | | | | | | | | |
| # Explants with Embryos | 0 | 0 | 0 | 35763 | 17/30 | 18/30 | 24/30 | 24/30 | 24/30 | 24/30 |
| % Explants with Embryos | 0 | 0 | 0 | 36.7 | 56.7 | 60% | 80% | 80% | 80% | 80% |
| Ruby Gold | | | | | | | | | | |
| # Explants with Embryos | 0 | 0 | 0 | 0 | 1/32 | 3/32 | 3/32 | 3/32 | 3/32 | 3/32 |
| % Explants with Embryos | 0 | 0 | 0 | 0 | 3.1% | 9.4% | 9.4% | 9.4% | 9.4% | 9.4% |
| Russet Burbank | | | | | | | | | | |
| # Explants with Embryos | 0 | 0 | 0 | 4/72 | 36/72 | 61/72 | 69/72 | 72/72 | 72/72 | 72/72 |
| % Explants with Embryos | 0 | 0 | 0 | 5.4% | 50% | 84.7% | 95.8% | 100% | 100% | 100% |
| Russet Norkotah | | | | | | | | | | |
| # Explants with Embryos | 0 | 0 | 0 | 36/129 | 82/129 | 96/129 | 102/129 | 106/127 | 111/127 | 111/127 |
| % Explants with Embryos | 0 | 0 | 0 | 27.9% | 63.6% | 77.5% | 79.1% | 83.4% | 87.4% | 87.4% |
| Saginaw Gold | | | | | | | | | | |
| # Explants with Embryos | 0 | 0 | 0 | 8/115 | 56/115 | 98/115 | 98/113 | 100/113 | 102/113 | 102/113 |
| % Explants with Embryos | 0 | 0 | 0 | 6.9% | 48.7% | 85.2% | 86.7% | 88.5% | 90.2% | 90.2% |
| Shepody | | | | | | | | | | |
| # Explants with Embryos | 0 | 0 | 0 | 2/120 | 2/120 | 6/120 | 6/120 | 8/120 | 8/120 | 11/120 |
| % Explants with Embryos | 0 | 0 | 0 | 1.7% | 1.7% | 5% | 5% | 6.7% | 6.7% | 9.2% |
| Superior | | | | | | | | | | |
| # Explants with Embryos | 0 | 0 | 18/121 | 102/121 | 121/121 | 121/121 | 121/121 | 121/121 | 121/121 | 121/121 |
| % Explants with Embryos | 0 | 0 | 14.9% | 84.3% | 100% | 100% | 100% | 100% | 100% | 100% |
| Temagami | | | | | | | | | | |
| # Explants with Embryos | 0 | 0 | 0 | 0 | 0 | 2/30 | 2/30 | 2/30 | 35518 | 35579 |
| % Explants with Embryos | 0 | 0 | 0 | 0 | 0 | 6.7% | 6.7% | 6.7% | 10% | 16.7% |
| Yukon Gold | | | | | | | | | | |
| # Explants with Embryos | 0 | 0 | 18/114 | 34/114 | 44/114 | 57/114 | 58/114 | 58/114 | 58/114 | 58/114 |
| % Explants with Embryos | 0 | 0 | 15.8% | 29.8% | 38.6% | 50% | 50.9% | 50.9% | 50.9% | 50.9% |

Potato clones vary in the time to produce somatic embryos (Table 3). The cultivars which readily form somatic embryos in culture; AC Novachip, Atlantic, Brador, Désirée, F80054, Kennebec, Russet Norkotah, Russet Burbank, Saginaw Gold and Superior (Table 3), generally produce somatic embryos on all of the explants in 3–4 weeks on medium #3. Notable exceptions were Ruby Gold and Temagami. Ruby Gold may require about 5 weeks to produce one or more explants out of forming somatic embryos. Temagami may require about six weeks to produce one or explants out of forming somatic embryos.

The mean number of somatic embryos produced per explant also may be under genotypic control. The rankings for the cultivars tested are expressed as mean number of somatic embryos per explant: F83065 (45), Désirée (36), Russet Burbank (28), F80054 (25), Brador (23), Royal Gold (17), Atlantic (16), Katahdin (14), AC Novachip (14), Superior (11), Russet Norkotah (11), Kennebec (10), Saginaw Gold (9), Caribe (7), Temagami (4), Ruby Gold (3), and Yukon Gold (2) (Table 2).

Chronological and Physiological Age of Stock Plantlets

The length of time to form somatic embryos in vitro and the number of embryos produced per explant appears to be partly determined by the vigour of the stock plantlets from which the explant tissues are excised. Without wishing to be bound by theory, a component of plantlet vigour may be the length of time since the last transfer to fresh medium and possibly the environmental regime in the tissue culture growth facility. Changes in the photoperiod, light quality, light intensity, or temperature regime may have effects on plantlet vigour.

Formation of Somatic Embryos on a Various Tissues

Somatic embryos have been formed on the following tissues cultured in vitro, stem internode explants, leaf blade tissue, roots and microtuber slices.

Secondary Embryos

Secondary embryos do not readily form in cultures of potato. Somatic embryos have been observed forming at the base of germinating embryos, at various stages of development. A scanning electron microscope study of the embryo forming cultures revealed that this was fairly uncommon (FIG. 1A to FIG. 1F).

Re-culture of Somatic Embryos

Potato somatic embryos at the torpedo, late torpedo and germination stages of development were re-cultured using the standard somatic embryogenesis protocol above. Some regeneration of new somatic embryos occurred at the basipetal end (root) of the re-cultured somatic embryos after nodular callus formation. Stem internode sections from germinating somatic embryos also have regenerated new somatic embryos. However, this process requires longer periods of time, for example, new somatic embryos have been observed after seven weeks of culture, compared with three to five weeks typically noted for somatic embryos production formed from cultured potato plantlet stem internode explants.

Size of Explant and Orientation of Explant in Medium

Upon transfer to medium #3, the stem internode explants are generally placed in the nutrient medium in a horizontal position, however, other positions may also be feasible. In this orientation the distal (the stem end away from the shot apex) end has been found to form more nodular callus than the proximal the stem surface closest to the shoot apex end of the stem explant. Somatic embryos have also been found to form on very thin slices of stem internode tissues, for example from about 0.05 mm to about 10 mm. The orientation of the explant, that is whether the distal or proximal end of stem piece is in the medium, affects productivity of somatic embryos from stem pieces.

Germination of Somatic Embryos to form Emblings'

An embling, is defined herein as a small plantlet grown from a somatic embryo. Frequently the early growth habit of an embling resembles that of a seedling.

Somatic embryos produced using the method of this invention are easily dissected from the explant tissue using any suitable means as would be evident to one of skill in the art. They are placed on medium #1 (described above) and germinated. The resulting embling resembles seedlings obtained from true seeds. For potato, emblings have a slightly viney habit, with thin stems and small leaves. Embryos at the early torpedo stage take about 2 to 4 weeks to become fully established emblings. The conversion of torpedo-shaped somatic embryos to emblings is easily accomplished, and no discernible alteration in growth of the plantlets is observed.

Apical dominance is apparent in many of the cultures. Frequently, clusters of proembryos, globular and heart-shaped embryos form at the base of a germinating somatic embryo.

Phenotypic Stability of Potato Regenerants

Germinating somatic embryos from potato cultivars Atlantic, Kennebec, Russet Burbank, Russet Norkotah, and Superior were excised and transferred to medium #1, containing no growth regulators. After 2–3 weeks, the emblings were acclimatized to greenhouse conditions and grown as greenhouse plants. These greenhouse plants were observed for differences in plant habit and morphology compared to sewed-grown plants. Minitubers (greenhouse tubers) were harvested and assessed for trueness-to-type.

Off-types have been reported from tissue culture regimes of potato (Harding, 1994, 1995). Similarly, some potato cultivars exhibited off-types as well. Furthermore, some cultivars displayed more off-types than others. Of the cultivars that displayed off-types, approximately 10 to 20 percent of the greenhouse plants exhibited this morphology. Generally, if the greenhouse plant showed aberrations, the minitubers harvested from that plant were also off-type. The presence of off-types appears to be influenced by genotype.

Somatic Embryogenesis of Tomato (*Lycopersicon esculentum* L) in vitro

Somatic embryos have been produced using juvenile tissue such as seedling hypocotyl or basal area of tomato requiring a 6 week protocol (Gill et al., 1995). However, somatic embryos have not been produced using other tissues. Using the method of this invention, somatic embryos have been produced on tomato using mature stem internode tissue. The method used involved Medium #2 with thidiazuron only for 1 week, followed by Medium #3 with zeatin, indole acetic acid and gibberellic acid for 4 weeks. Somatic embryos are observed within a 4 week period.

All three genotypes tested (Big Beef, Cheyenne, and Viva Italia) produce somatic embryos on stem internode tissues. Some genotypic differences in reaction to the tissue culture protocol are observed. Generally more callus formation is observed on tomato tissues compared with potato. The following table (Table 4) outlines the differences in method described herein with the prior art method of Gill et al. (1995).

TABLE 4

Comparison of the method of this invention with the prior art for the production of somatic embryos of *Tomato Lycopersicon esculentum* L. in vitro

| | Method of this invention | Gill et al. (1995) |
|---|---|---|
| Cultivars regenerated | Big Beef, Cheyene, Viva Italia | Campbell 1327VF, Crimsonvee VF, Glamour, MH 6208, Red Robbin, Scocet Million, Sweet Million |
| Explant cultured | Tissue culture plantlet, stem internode | Intact seeding, hypocotyl or basal area |
| Genotypic difference in response to culture conditions | Yes | Yes |
| Tissue culture protocol | Two step somatic embryogenesis protocol* | One step protocol with MS medium + BAP |
| Time to produce | from 4 to 6 weeks | 6 weeks |
| Environmental protocol | 16 hour photoperiod | |

*Medium # 2 with thidiazuron only - 1 week
Medium # 3 with zeatin, indole acetic acid and gibberellic acid - 4 weeks Somatic Embryogenesis of Lettuce (*Lactuca sativa* L.) in vitro Somatic embryogenesis of lettuce has been reported by Zhou et al. (1992) using seedling cotyledons in vitro. The disadvantage of this technique is that there is considerable variability (heterosis) in the morphology of the propagated material, and such variability is not commercially acceptable in lettuce. Therefore, material propagated from seedling tissues is of uncertain advantage commercially. A clonal propagation technology for lettuce is of great interest to the lettuce industry because currently growers have to rogue out off-types which are not commercially acceptable, and this can be a considerable portion of the crop. Furthermore, lettuce somatic embryos lend themselves to synthetic seed technology and fluid drilling of the synseeds for a clonally propagated crop which reduced the need for field roguing.

The method of this invention produced somatic embryos using mature lettuce tissues obtained from stem internode, mature leaves, or axllary buds. The method employed using maintaining the tissue of medium #1 for 1 week, followed by medium #2c (i-e. containing BAP and IAA) for two weeks. Following this protocol, somatic embryos are observed withiin 3 weeks, compared to 7 weeks with the prior art protocol. A comparison of the method of this invention with that of Zhou et al. (1992) is outlined in Table 5.

TABLE 5

Comparison of the method of this invention with that of the prior art, for the production of somatic embryos of Lettuce (*Lactuca sativa* L.) in vitro

| | Method of this invention | Zhou et al. (1992) |
|---|---|---|
| Cultivars Regenerated | Butter Crunch, Grand Rapids, Red sails | Lettuce - no cultivar name provided |
| Explant Cultured | - Seedling (10 day old) stem internode and leaves in vitro<br>- Excised axillary buds from mature, greenhouse-grown 'Red Sails plant. Bud established in vitro; leaves (occasionally stem internode) of cultured plantlet used as explants. | Seedling cotyledons in vitro |
| Genotypic Differences | Some genotypic differences in reaction to media observed, although all cvs. Tested produced somatic embryos. | Not stated. |
| Tissue Culture Protocol | Two step somatic embryogenesis protocol*. 16 hour photoperiod | Callus induction in dark (4 weeks), transfer to light on same medium for 3 weeks for somatic embryos to form. MS salts, BAP & NAA |
| Time to Produce Somatic Embryos | Three Weeks | Seven Weeks |

*Medium # 1 for 1 week, followed by 2 weeks on medium #2c.

The present invention has been described with regard to preferred embodiments. However, it will be obvious to persons skilled in the art that a number of variations and modifications can be made without departing from the scope of the invention as described herein.

References

Bajaj, Y. P. S. 1995a. Somatic embryogenesis and its applications for crop improvement. Chapter II1.1. In: Biotechnology in Agriculture and Forestry. 30. Somatic Embryogenesis and Synthetic Seed. I. (Ed: Y. P. S. Bajaj). Springer-Verlag :105–125.

Bajaj, Y. P. S. 1995b. Cryopreservation of somatic embryos. Chapter II.8. In: Biotechnology in Agriculture and Forestry. 30. Somatic Embryogenesis and Synthetic Seeds. Springer-Verlag: 221–229.

Bragdø-Aas, M. 1977. Regeneration of Plants from callus of potato plants. Acta Horticulturae. 78:133–137.

Chen, L.-Z. and T. Adachi. 1994. Plant regeneration via somatic embryogenesis from cotyledon protoplasts of tomato (*Lycopersicum esculentum* Mill.). Breeding Science. 44: 257–262.

D'Onghia, A. M., F. de Pasquale, F. Carimi, V. Savino and F. G. Crescimanno. 1997. Somatic embryogenesis for style culture as a possible means for virus elimination in *Citrus*. J. Phytopathology. 145: 77–79.

Ellis, D. 1995. Genetic Transformation of somatic embryos. In: Biotechnology in Forestry and Agriculture. 30. Somatic Embryogenesis and Synthetic Seed. I. (Ed: Y. P. S. Bajaj). II.7:207–220.

Garcia, E. de, S. Martinez. 1995. Somatic embryogenesis in *Solanum tuberosum* L. cv. Désirée from stem nodal sections. J. Plant Physiology. 145: 526–530.

Gill, R., K. A. Malik, M. H. M. Sanago, an P. K. Saxena. 1995. Somatic embryogenesis and plant regeneration from seedling cultures of tomato (*Lycopersicum esculentum* Mill.). J. Plant Physiol. 147:273–276.

Gray, D. J., M. E. Compton, R. C. Harrell and D. J. Cantliffe. 1995. Somatic Embryogenesis and the Technology of Synthetic Seed. In: Biotechnology in Agriculture and Forestry. 30. Somatic Embryogenesis and Synthetic Seed. I. II.2:126–151.

Litz, R. E. and D. J. Gray. 1995. Somatic Embryogenesis for agricultural improvement. World J. Microbiol.-Biotechnol. 11(4):416–425.

Linsmayer and Skoog. 1965. Plant Physiol 18.

Mathews, H., R. E. Litz, H. D. Wilde, S. A. Merkle and H. Y. Wetzstein. 1992. Stable integration and expression of b-glucuronidase and NPT II genes in mango somatic embryos. In Vitro Cell Dev. Biol. 28:172–178.

Murashige, T. and F. Skoog. 1962. A revised medium for rapid growth and bioassays with tobacco tissue cultures. Physiologia Plantarum. 15: 473–497.

Neuhaus, G. G. Spangenberg, 0. Mittelsten Scheid, H. G. Schweiger. 1987. Transgenic rapeseed plants obtained by the microinjection of DNA into microspore-derived embryos. Theor. Appl. Genet. 75:30–36.

Pretova, A. and B. Dedicova. 1990. Somatic embryogenesis from unripe *Solanum tuberosum* (cv. Désirée embryos. VIII Intl. Congress on Plant Tissue and Cell Culture. Abstract #B4-97: 265.

Redenbaugh, K. (ed.). 1992. Synseeds. Applications of synthetic seeds to crop improvement. CRC Press. Boca Raton. 481.

Redenbaugh, K., J. Fujii, D. Slade, P. Vis and M. Kossler. 1991. Artificial seeds—encapsulated somatic embryos. In: Biotechnology in Agriculture and Forestry. 17. II. (Ed: Y. P. S. Bajaj). III3.3:395–416.

Scorza, R., J. M. Cordts, D. J. Gray, D. Gonsalves, R. L. Emershad, D. W. Ramming. 1996. Producing transgenic Thompson Seedless' grape (*Vitis vinifera* L.) plants. J. Amer. Soc. Hort. Sci. 121(4):616–619.

Senaratna, T. 1992. Artificial seeds. Biotechnol. Adv. 10(3): 379–392.

Wilde, H. D., R. B. Meagher and S. A. Merkle. 1992. Expression of foreign genes in transgenic yellow-poplar plants. Physiol. 98: 114–120.

Zhou, X., Y. Han, W. Yang and T. Xi. 1992. Somatic embryogenesis and analysis of peroxidase in cultured lettuce (*Lactuca sativa* L.) cotyledons. Ann. Bot. 69:97–100.

What is claimed is:

1. A method for producing somatic embryos on potato plant tissue obtained from a non-juvenile plant comprising:
  i) obtaining a stock tissue culture plantlet by exposing potato plant tissue obtained from a non-juvenile plant to a growth regulator-free medium comprising salts, vitamins and an energy source;
  ii) preparing an explant from the stock tissue culture plantlet;
  iii) transferring the explant to a proliferation medium comprising salts, vitamins, an energy source and at least one growth regulator selected from the group consisting of a cytokinin or a cytokinin-like compound; and Indole acetic acid combined with said cytokinin or cytokinin-like compound, for about 3 days to less than 4 weeks, sufficient to produce a callused explant; and
  iv) transferring the callused explant to a medium comprising salts, vitamins, an energy source and at least two growth regulators comprising at least one auxin and at least one cytokinin or cytokinin-like compound for a period of time sufficient to produce somatic embryos.

2. The method of claim 1 wherein, the stock tissue culture plantlet is maintained in the medium of step i) from about 2 to about 20 weeks.

3. The method of claim 2 wherein, the period of time in step iv) is from about 2 to about 6 weeks.

4. The method of claim 1 wherein the cytokinin or cytokinin-like compound of the proliferation medium of step iii) is selected from the group consisting of Thidiazuron and BAP.

5. The method of claim 1, wherein the growth regulators of the medium of step iv) are selected from the group consisting of Zeatin and Indole acetic acid; and a combination of Zeatin, Indole acetic acid and Gibberellic acid.

6. The method of claim 1 wherein the explant is selected from the group consisting of stem internode, root, leaf, and microtuber tissue.

7. The method of claim 1 wherein the somatic embryo obtained from step iv) is grown into a plant.

8. The method of claim 1, wherein the stock tissue culture plantlets are maintained on a Medium #1 comprising:

| Murashige and Skoog salts, full strength | |
|---|---|
| sucrose | 30 g/l |
| myo-inositol | 100 g/l |
| vitamins | |
| Nicotinic acid | 0.5 mg/l |
| Pantothenic acid | 2.5 mg/l |
| Pyridoxine.HCl | 1.0 mg/l |
| Thiamine.HCl | 0.5 mg/l |
| pH 5.8 | |
| agar | 8 g/l; | the proliferation medium, medium #2, comprises:

| Murashige and Skoog salts, full strength | |
|---|---|
| sucrose | 30 g/l |
| myo-inositol | 100 g/l |
| vitamins | |
| Nicotinic acid | 0.5 mg/l |
| Pantothenic acid | 2.5 mg/l |
| Pyridoxine | 1.0 mg/l |
| Thiamine.HCl | 0.5 mg/l |
| pH 5.8 | |
| agar | 6.5 g/l; | and further comprises the constituents selected from the group consisting of;

| Medium 2a: | |
|---|---|
| Thidiazuron | 0.15 µM |
| Indole acetic acid | 19 µM |
| Medium 2b | |
| Thidiazuron | 0.15 µM [mg/l]; |
| Medium 2c | |
| BAP | 0.15 µM |
| IAA | 19 µM; and |
| Medium 2d | |
| BAP | 0.15 µM; and | the medium of step iv), medium #3, comprises:

| Murashige and Skoog salts, full strength | |
|---|---|
| sucrose | 30 g/l |
| myo-inositol | 100 mg/l |
| vitamins | |
| nicotinic acid | 1.0 mg/l |
| thiamine.HCl | 0.5 mg/l |
| pantothenic acid | 0.5 mg/l |
| pyridoxine | 1.0 mg/l |
| Zeatin | 12.0 µM |
| Indole acetic acid | 0.05 µM |
| Gibberellic acid | 0.55 µM |
| pH 5.8 | |
| agar. | 8 g/l |

9. A method of maintaining a potato plant comprising a desired set of characteristics comprising:

i) screening a library of potato plants for a desired set of characteristics;

ii) selecting a potato plant having the desired set of characteristics;

iii) preparing a somatic embryo, from tissue obtained from the selected plant of step ii), using the method of claim 1; and iv) either preserving the somatic embryo, or growing the somatic embryo into a potato plant.

* * * * *